(12) United States Patent
Hansen et al.

(10) Patent No.: US 7,611,849 B2
(45) Date of Patent: Nov. 3, 2009

(54) ENHANCED CELLULAR ASSAY METHOD FOR USE IN FLOW CYTOMETRY OR SIMILAR INSTRUMENTS USING OPTICALLY RESONANT PARTICLES

(75) Inventors: W. P. Hansen, Canaan, NY (US); Petra B. Krauledat, Canaan, NY (US)

(73) Assignee: Point Care Technologies, Marlborough, MA (US)

( * ) Notice: Subject to any disclaimer, the term of this patent is extended or adjusted under 35 U.S.C. 154(b) by 398 days.

(21) Appl. No.: 10/856,284

(22) Filed: May 27, 2004

(65) Prior Publication Data

US 2004/0246480 A1 Dec. 9, 2004

Related U.S. Application Data

(60) Provisional application No. 60/473,732, filed on May 27, 2003.

(51) Int. Cl.
| | |
|---|---|
| *G01N 21/00* | (2006.01) |
| *G01N 33/53* | (2006.01) |
| *G01N 33/543* | (2006.01) |
| *G01N 33/553* | (2006.01) |
| *G01N 33/563* | (2006.01) |

(52) U.S. Cl. .................. 435/7.2; 435/7.24; 436/518; 436/519; 436/520; 436/521; 436/523; 436/524; 436/525; 422/82.05

(58) Field of Classification Search .................. 435/7.2, 435/7.24; 436/518–525, 164, 172
See application file for complete search history.

(56) References Cited

U.S. PATENT DOCUMENTS

| | | | |
|---|---|---|---|
| 4,284,412 A | | 8/1981 | Hansen et al. |
| 5,538,893 A | * | 7/1996 | Sakata et al. .................. 436/10 |
| 5,547,661 A | * | 8/1996 | Sun et al. ...................... 424/66 |
| 5,939,021 A | | 8/1999 | Hansen et al. |
| 6,413,786 B1 | | 7/2002 | Hansen et al. |
| 2005/0244816 A1 | * | 11/2005 | Valdez .......................... 435/5 |

FOREIGN PATENT DOCUMENTS

JP          64000208 A   *  1/1989

OTHER PUBLICATIONS

Siiman et al., "Immunophenotyping using gold or silver nanoparticle-polystyrene bead conjugates with multiple light scatter," Cytometry, 2000, vol. 41, pp. 298-307.*

(Continued)

*Primary Examiner*—Unsu Jung
(74) *Attorney, Agent, or Firm*—Edwards Angell Palmer & Dodge LLP; George W. Neuner; Gregory B Butler, Esq.

(57) ABSTRACT

This invention relates to the field of biological assays where cells can be classified and enumerated using flow cytometry optical instrumentation. The invention combines information from multi-angle, light scatter from the cell itself and multi-angle light scatter from small, optically resonant particles that are selectively bound to surface molecules on the cell to carry out classification and enumeration. This light scatter method enables an instrumentation system that is simple to use, inexpensive to build, and mechanically robust; making it suitable for use in remote clinical environments.

2 Claims, 12 Drawing Sheets

OTHER PUBLICATIONS

You et al., "Surfactant-mediated gene transfer for animal cells," Cytotechnology, 1997, vol. 25, pp. 45-52.*

Siiman O. "Preparation, Microscopy, and Flow Cytometry with Excitation into Surface Plasmon Resonance Bands of Gold or Silver Nanoparticles on Aminodextran-Coated Polystyrene Beads" J. Phys. Chem. B 2000, vol. 104, pp. 9795-9810.

Gailene R. Gabel. International Search Report for PCT/US04/16855 Aug. 18, 2006.

* cited by examiner

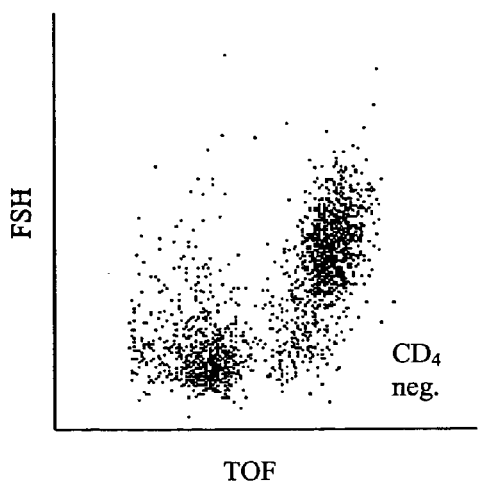
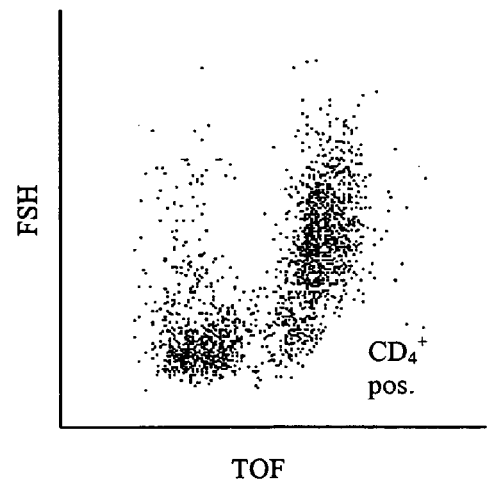
Figure9a.
Figure9b.

ENHANCED CELLULAR ASSAY METHOD FOR USE IN FLOW CYTOMETRY OR SIMILAR INSTRUMENTS USING OPTICALLY RESONANT PARTICLES

PRIORITY

The present application claims priority to U.S. Provisional Application No. 60/473,732, filed May 27, 2003.

FIELD OF THE INVENTION

This invention relates to the field of biological assays where cells can be classified and quantified using flow cytometry and other optical instrumentation.

BACKGROUND

Selective binding of polystyrene particles, gold particles, silver particles, as well as polystyrene particles coupled to gold and silver particles have been used to identify cell types in a laser flow cytometer by light scatter rather than by fluorescence (Bohmer, King. *Journal of Immunologic Methods*, "Immuno-Gold Labeling for Flow Cytometric Analysis. 74(1984)49-57; Bohmer, King. *Cytometry*, "Flow Cytometric Analysis of Immunogold Cell Surface Label. 5(1984)543-546; Festin, Bjorklund. Journal of Immunological Methods, "Detection of Triple Antibody-binding Lymphocytes in a Standard Laser Flow Cytometry using Colloidal Gold, Fluorescein and Phycoerythrin as Labels". 101(1978) 23-28). While a light-scatter laser flow cytometer is simpler, more durable, and significantly less expensive to manufacture than a fluorescence flow cytometer, these prior art light scatter assay methods need several complex user steps or expensive manufacturing steps to enhance the light scatter signal, and create a detectable signal over background light scatter from the cells themselves.

The need for multiple steps by a skilled user and/or the high cost of manufacture, prevents these prior art particle binding assays from being used in resource-poor environments where highly trained laboratory technicians are not widely available, and health care is poorly financed. Within the industrialized nations, eliminating the need for a highly trained laboratory technicians and reduced manufacturing cost is desired for health care cost containment.

SUMMARY OF THE INVENTION

The present invention uses the combination of the inherent, multi-angle light scatter from cells and the multi-angle light scatter from small particles that are selectively bound to surface molecules that are characteristic of the cell to identify and quantify cells in liquid suspension. The present invention uses methods of signal enhancement from light scatter particle labels that make the assay simple to use and inexpensive to manufacture, and novel flow cytometry apparatus that combines the particle label multi-angle light scatter signal with the inherent light scatter signal from the cell to positively identify and quantify the cell type.

The invention uses particle materials that exhibit abnormally high light scattering efficiencies at certain "resonance wavelengths" (Optically Resonant Particles, ORP's) (Bohren and Huffman, *Absorption and Scattering of Light by Small Particles*, Wiley Interscience, 1983.). This resonance can greatly enhance the signal strength and enable a more sensitive cell identification assay. Unfortunately, these resonance wavelengths and available laser wavelengths are not always the same. The invention teaches a method of using ORP size to "tune" the resonance wavelength and strength of the resonance simultaneously to an optimum relative to the laser wavelength.

As such, the present invention relates to a method for the detection of an Optically Resonant Particle (ORP) by light scattering comprising the simultaneous optimization of the resonance wavelength and strength of resonance of the ORP to the laser excitation wavelength, whereby the resonance wavelength can be modified by increasing or decreasing the size of the ORP.

Second, the present invention teaches a method of chemically accelerating the particle binding reaction to produce a detectable signal on a light scatter flow cytometer without centrifuging or "vortex" mixing the sample and reagent. Surface charge must be maintained in order to store a colloidal suspension for later use, but when this particle surface charge and the cell surface charge are of the same sign, then mechanical means such as centrifugation or manual "vortex" mixing have been used to force the particles and cells into contact. (Joe Tien, Andreas Terfort, and George M. Whitesides, *Microfabrication Through Electrostatic Self-Assembly, Langmuir* 1997, 13, 5349-5355) The method of the present invention relies on changing the surface charge characteristics of the particle and the cells in the sample by chemical means that are low cost and do not rely on the manual skill of the operator.

As such, the present invention relates to a method of decreasing the Coulombic forces between cell surface receptors and ORP's comprising the treatment of a sample containing cell surface receptors and ORP's with a cationic surfactant, wherein the cationic surfactant can be selected from the group consisting of decamethonium bromide, polydiallyldimethylammonium chloride and hexadecyltrimethylammonium bromide.

Third, the present invention teaches multi-angle light scatter flow cytometry apparatus that combines light scatter from the cell itself with light scatter signal from the particles that are bound to the cell surface to make Boolean logic judgements as to the biological identity of cells, and count only those that satisfy certain logical conditions (see U.S. Pat. No. 4,284,412). Light scatter angles not sensitive to ORP's but otherwise sensitive to the inherent light scatter properties of cells are used to gate a flow cytometer on certain classes cells and light scatter angles sensitive to ORP's are used to identify and quantify sub-classes of said classes of cells.

As such, the present invention relates to a method for the identification and quantification of cells using a flow cytometer that employs the combination of inherent, multi-angle light scatter from cells and multi-angle light scatter from Optically Resonant Particles (ORP's) conjugated to cell specific binding compounds that selectively bind to surface structures characteristic of specific cells.

As a general example of the present invention, where CD4 positive, human T-lymphocytes are identified and quantified in a whole blood sample. The light scatter signal from colloidal gold particles is optimized for maximum strength by size selection according to the laser wavelength used for detection. They are conjugated with anti-CD4 monoclonal antibodies and reacted with human whole blood using a reaction buffer that neutralizes particle surface charge and accelerates the reaction without the need for centrifugation or manual "vortex" mixing. Finally, a multi-angle light scatter apparatus is described and used to distinguish and count lymphocytes bearing the CD4 surface marker from monocytes that also bear the CD4 surface marker, or interfering granulocytes with similar light scatter signals, thus making the method and apparatus valuable for monitoring the concentration of CD4 positive T-lymphocytes in HIV-infected patients. This is a key diagnostic parameter in AIDS therapy management. Other examples are offered for the detection of other cell subsets.

The present invention uses a simple assay that is inexpensive to automate and inexpensive to manufacture. The invention uses reagents that have an inherently low manufacturing cost while providing a strong signal that can be analyzed automatically without the need for a skilled flow cytometry operator exercising human judgment to separate the signal from background. Applications for the present invention include AIDS antiretroviral therapy monitoring in resource poor parts of the world and in remote public health centers in the industrialized world.

BRIEF DESCRIPTION OF THE FIGURES

FIG. 9 are diagrammatic representations of comparative positions of lymphocyte clusters (a) using FSH versus TOL with a nonbonding control reaction with colloidal gold and (b) using FSH versus TOL when anti CD4 conjugated colloidal gold binds to the lymphocyte surface.

DETAILED DESCRIPTION OF THE INVENTION

This invention relates to the field of biological assays where cells can be classified and enumerated using flow cytometry optical instrumentation. The invention combines information from multi-angle, light scatter from the cell itself and multi-angle light scatter from small, optically resonant particles that are selectively bound to surface molecules on the cell to carry out classification and enumeration. This light scatter method enables an instrumentation system that is simple to use, inexpensive to build, and mechanically robust; making it suitable for use in remote clinical environments.

A. Optical Resonance and Methods of Optimizing the Detection ORP's:

The present invention uses small particles that are chemically pre-conjugated to molecules, such as antibodies, that bind selectively to sites on the surface of cells. The characteristic light scatter pattern of the cell is modified by the bound particles and this modification can be detected by the use of a microscope, a flow cytometer, a spectrophotometer or other similar optical instrumentation. Flow cytometry is the preferred embodiment of the present invention.

Optically small particles are particles that are smaller than the wavelength of the incident light. When the refractive index of the particles has both real and imaginary parts, $N=(n+ik)$, the particle not only scatters light, but it also absorbs light.

The amount of light scattered or absorbed by a particle is, in part, proportional to its geometric cross-sectional area, G. For a spherical particle, $G=\pi a^2$, where a is the particle radius. In addition to this geometrical factor, the amount of light scattered or absorbed is a function of wavelength. Most particles have real and imaginary parts of the refractive index that are not in themselves strong functions of wavelength. Under these common conditions, the wavelength dependence for scattering and absorption is simple. Scattering is proportional to $\lambda^{-4}$ and absorption is proportional to $\lambda^{-1}$.

Figure 1:
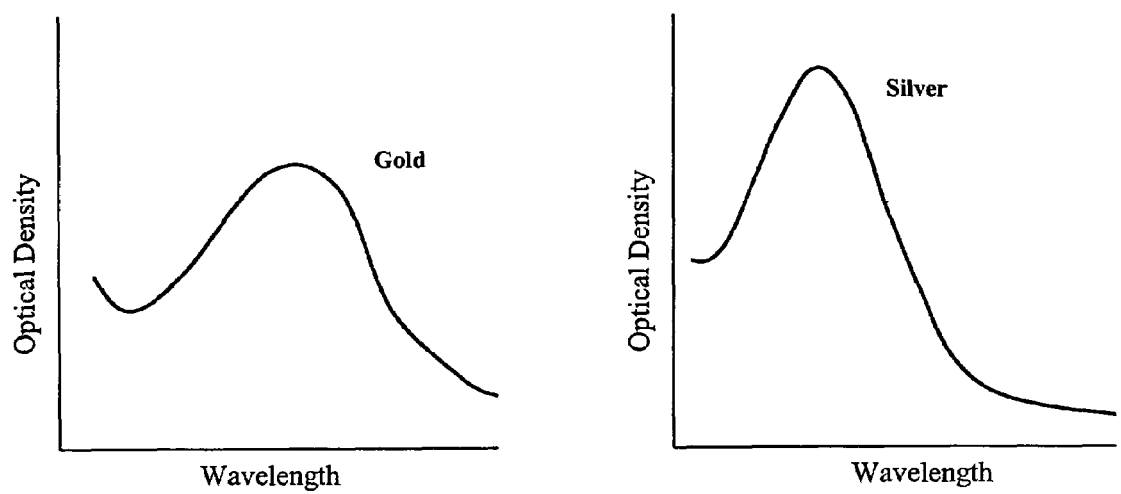
FIG. 1 contains diagrammatic representations of optical resonance for 40 nm gold particles and 40 nm silver particles in colloidal suspension.

Some small particles have real and imaginary parts of the refractive index, $N=(n+ik)$, that are strong functions of wavelength, $\lambda$. Under certain conditions, the scattering efficiency and absorption efficiency can depart significantly from the simple wavelength laws of $\lambda^{-4}$ and $\lambda^{-1}$, and become abnormally high and reach a local maximum at a "resonance wavelength" $\lambda_R$. This occurs when the real part, $n(\lambda)$, approaches 0, and the imaginary part, $k(\lambda)$, approaches $\sqrt{2}$, at a wavelength $\lambda_R$ (Bohren and Huffman, *Absorption and Scattering of Light by Small Particles*, Wiley Interscience, 1983.). Such particles are called ORP's or Optically Resonant Particles (FIG. 1).

The resonance wavelength and relative strength of the resonance are also functions of the size of the particle. As the particle size approaches zero the resonance wavelength approaches a minimum value and a maximum relative strength that is dependent on the particle material. Examples of resonant particle materials and their associated minimum resonance wavelengths are aluminum at ~200 nm (ultraviolet), silver at ~400 nm (visible), gold at ~530 nm (visible), and silicon carbide at ~10 microns (infrared). As the particle size increases, the resonance wavelength increases but the relative strength of the resonance decreases (Bohren and Huffman, *Absorption and Scattering of Light by Small Particles*, Wiley Interscience, 1983.). This makes overall light scatter and absorption dependent on two size factors, the geometrical cross section, G, and the size-dependent position and relative strength of the resonance wavelength.

The following is an example of how these factors are used in the present invention to optimize light scatter for a particular laser excitation. The silver particle resonance in the small particle limit is at ~400 nm and agrees exactly with a semiconductor diode laser wavelength (see U.S. Pat. No. 6,413, 786, hereby incorporated by reference in its entirety). Unfortunately, with today's technology this laser is expensive and not reliable. Gold can also be used to make optically resonant particles (Bohren and Huffman, *Absorption and Scattering of Light by Small Particles,* Wiley Interscience, 1983.) and gold has advantages over silver in that the attachment of binding molecules to gold is very straightforward. The gold resonance at ~530 nm agrees exactly with another laser that is also expensive and unreliable. But the gold resonance wavelength can be tuned upward toward 635 nm where an inexpensive, durable, and very reliable semiconductor laser emits light.

Figure 2:
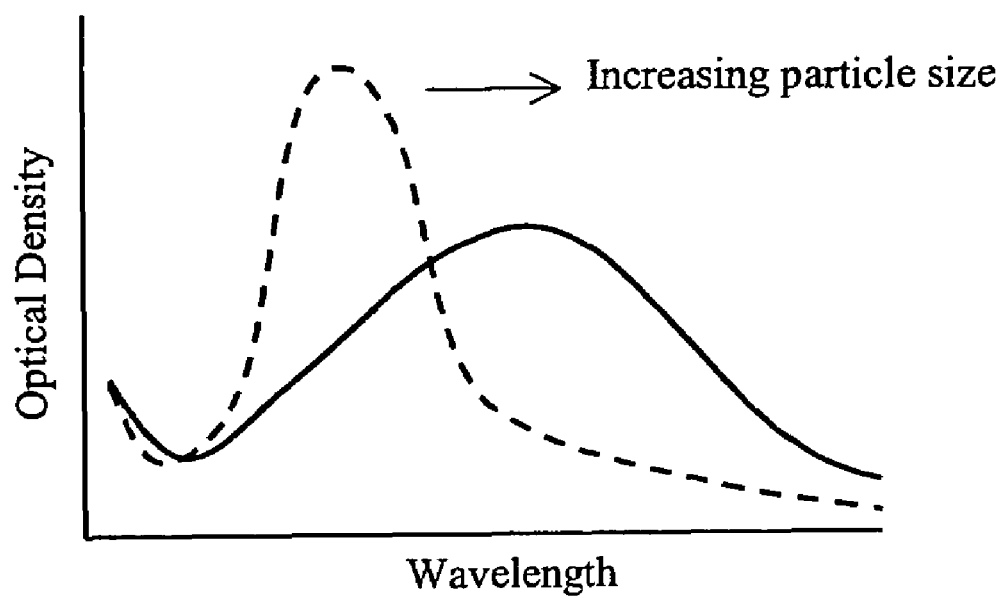
FIG. 2 is a diagrammatic representation of tuning an optical resonance to a longer wavelength by increasing particle size.

The upward tuning of the gold resonance toward 635 nm works only over a defined particle size range. This size range is determined as follows. The resonance maximum shifts to longer wavelengths as the particle size increases. This increases light scatter at longer wavelengths. Light scatter increases as the geometric cross section of the particle increases. However as the resonance maximum shifts to longer wavelengths, the strength of the maximum decreases, which tends to decrease light scatter. These competing factors can produce an optimum particle size. This effect is illustrated in FIG. 2.

Figure 3:
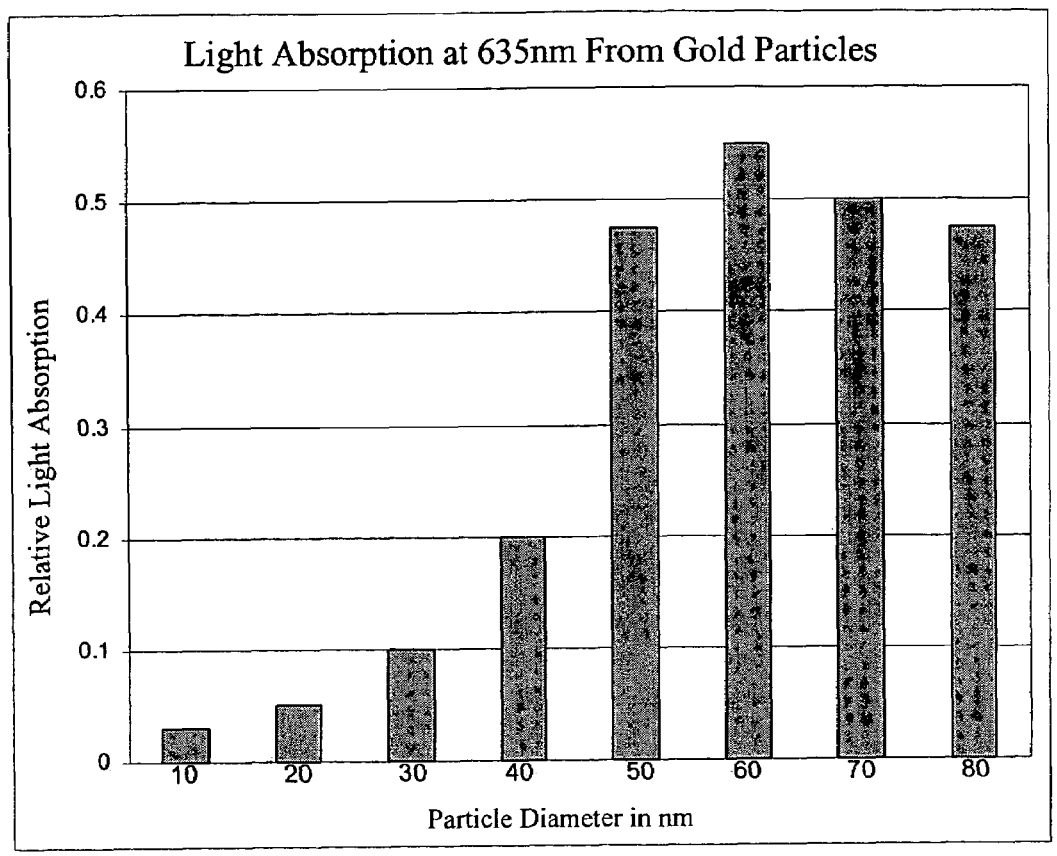
FIG. 3 is a bar graph representation of light absorption from gold particles as a function of particle size.

The optimum size is demonstrated in FIG. 3. Gold sols with relatively monodisperse diameters were analyzed in a spectrophotometer. Relative, light absorption intensity at 635 nm was plotted versus gold particle size for each sol. The optimum size is seen to be near 60 nm or slightly greater where there is a peak for light absorption intensity. Where there are peaks in absorption, there will be peaks for light scatter with ORP's. This is demonstrated in the next example where light scatter from cells was recorded in a multi-angle flow cytometer using particles sizes in the vicinity of the peak shown in FIG. 3.

Figure 4:
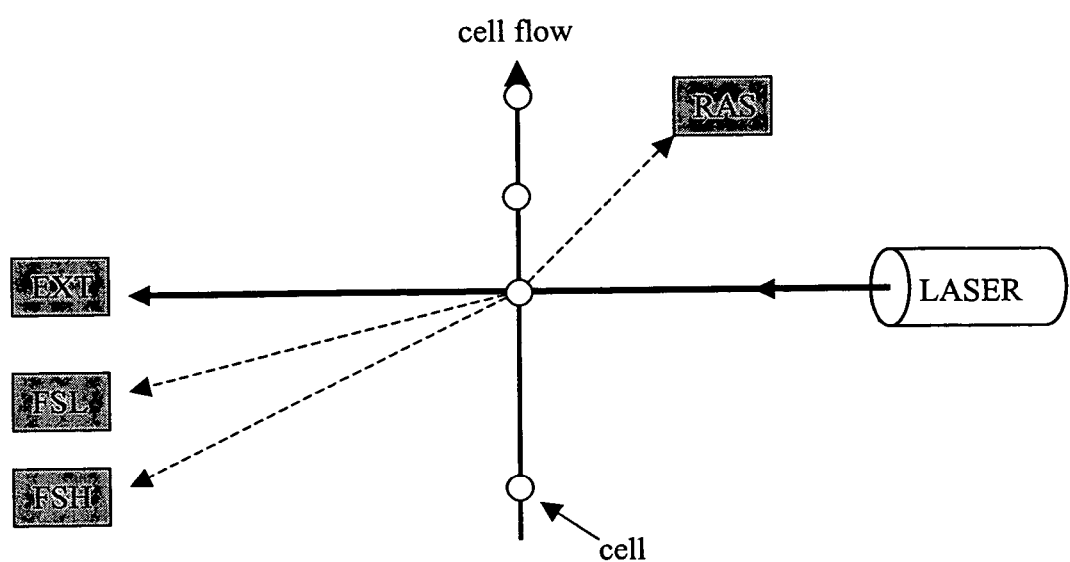
FIG. 4 is a schematic illustration of a multi-angle light scatter flow cytometer; including sensors for extinction (EXT), low angle forward scatter (FSL), high angle forward scatter (FSH) and right angle scatter (RAS).
Figure 5A:
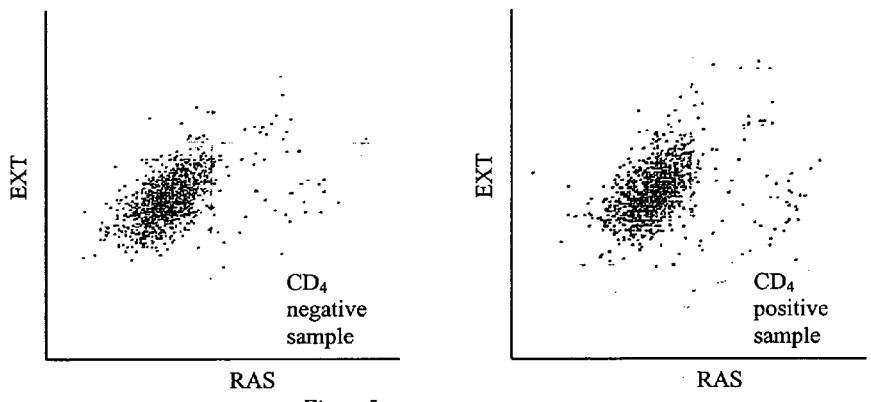
FIG. 5 represents the results of light scatter flow cytometric analysis with a semiconductor diode laser at a wavelength of 635 nm for gold particles with sizes of 40 nm (a), 80 nm (b) and 100 nm (c).
Figure 5B:
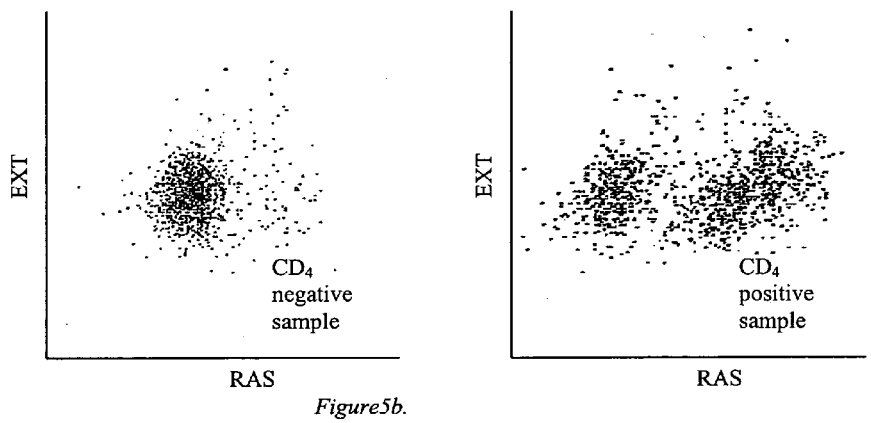
Figure 5C:
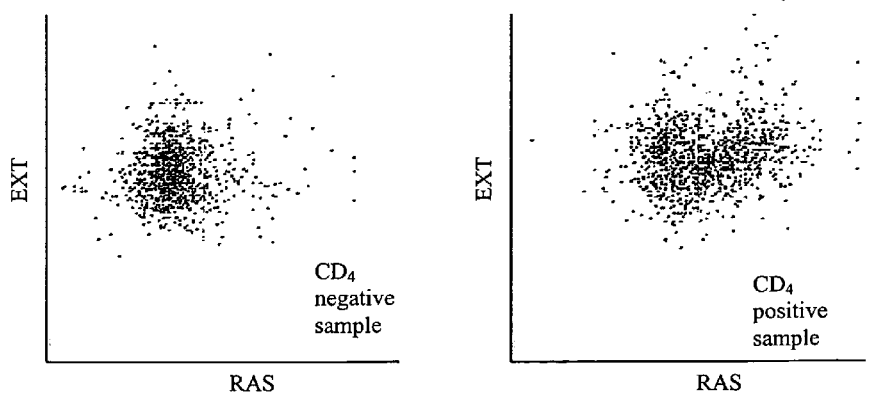

Three sizes of gold particle were used to label cells and were analyzed by a light-scatter flow cytometer with a semiconductor diode laser at a wavelength of 635 nm (FIG. 4). The particle sizes were 40 nm, 80 nm, and 100 nm. With 40 nm particles the labeling of lymphocytes was undetectable (FIG. 5a). With 80 nm particles, the gold labeled lymphocytes were clearly detectable as a second dot cluster shifted to the right (FIG. 5b). With 100 nm particles, the second cluster was clearly detectable, but the shift to the right was less than with 80 nm particles (FIG. 5c). This is in agreement with the graph of FIG. 3, suggesting that optimal light scatter occurs for a particle size between 40 nm and 100 nm.

Figure 6:
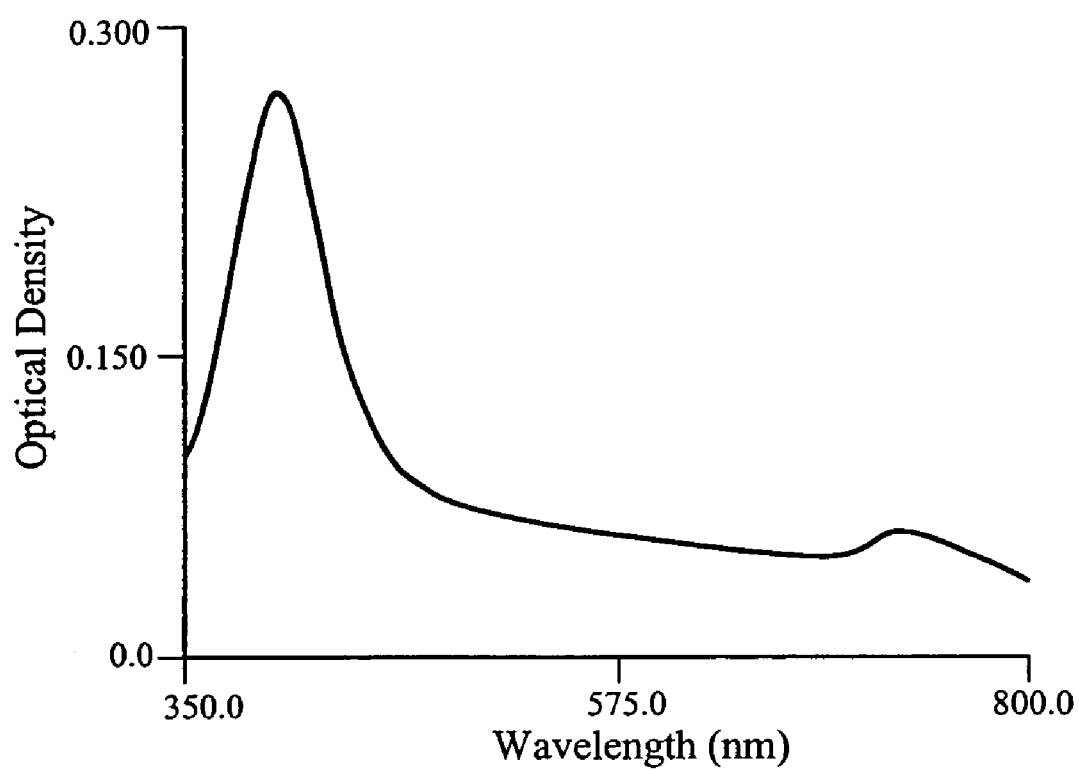
FIG. 6 is a diagrammatic representation of an absorption spectrum of 50 nm silver colloids with resonance peak at 423 cm.

Example of Resonance Optimizing the Resonance Wavelength Downward:

In this example, 50 nm silver particles were suspended in water and shown to resonate at 442 nm (FIG. 6). A semiconductor diode laser exists at 400 nm. Decreasing the particle size will shift the silver resonance downward and will increase the strength of the resonance. Both of these effects will increase light scatter. The geometric cross section will decrease, which will tend to lower light scatter. Using the same experimental technique that was outlined for determining the optimum increase in gold particle size, one can experimentally determine the optimal particle size decrease to produce maximum light scatter from a 400 nm diode laser with silver.

Other Examples of Optically Resonant Materials Capable of Optimization

These techniques can be extended to any optically resonant particle regardless of its composition. For example, the same principles apply to metallic elements (gold and silver in the visible spectrum), compounds (silicon dioxide in the near infrared spectrum), and semiconductors (silicon carbide in the middle infrared spectrum).

Preference for Light Scatter Over Fluorescence

Light scatter labels are to be preferred over fluorescent labels for reasons of instrumentation stability, cost and ease of use. Fluorescent light in flow cytometers must be collected and, most importantly, collimated so as to strike the surface of costly, multilayer dielectric filters within approximately 2 degrees of perpendicularity. If this condition is not met, then the transmission characteristics of the filter change significantly. When this happens, laser light is inadvertently transmitted to the photomultiplier sensor and fluorescence detection is rendered impossible due to high background. It is well-known in the art that maintaining optical alignment of the collimating lenses and filters in a fluorescence flow cytometer is difficult, requiring frequent field adjustment and a costly mechanical design that allows adjustment. With light scatter, filters are not needed; hence the collimating lenses can be eliminated. Under these conditions, simple silicon photodiodes can be rigidly mounted together with the flow cytometer flow cell, with no adjustment mechanism required.

B. Particle Binding Kinetics of ORP's to the Cell Surface and Methods of Overcoming Coulombic Forces:

Consider a small particle in liquid suspension that moves by predominantly by Brownian motion and is smaller than a cell. Let this particle be coated with a molecule that selectively binds to characteristic receptors on the surface of a cell type. For example, the particle could be a metal colloidal sol, the selectively binding molecule could be an antibody, and the characteristic receptor could be an antigen to that antibody.

In prior art methods the rate at which antibody-coated colloidal metal particles bind to cell surface receptors was enhanced by centrifugation or manual vortex mixing (Bohmer, King. *Journal of Immunologic Methods,* "Immuno-Gold Labeling for Flow Cytometric Analysis. 74(1984)49-57; Bohmer, King. *Cytometry,* "Flow Cytometric Analysis of Immunogold Cell Surface Label. 5(1984)543-546; Festin, Bjorklund. Journal of Immunological Methods, "Detection of Triple Antibody-binding Lymphocytes in a Standard Laser Flow Cytometry using Colloidal Gold, Fluorescein and Phycoerythrin as Labels". 101(1978) 23-28; Olvai Siiman, Kristie Gordon, Alexander Burshteyn, John A. Maples, and James K. Whitesell. Cytometry, "Immunophenotyping Using Gold or Silver Nanoparticle-Polystyrene Bead Conjugates With Multiple Light Scatter". 41:298-307 (2000)). Both methods have similar physical principles at their foundation. Centrifugation creates a relative motion between the particle sol and the cell as the cell is driven toward the bottom of the centrifuge tube by the "g" force. The cell sweeps out a path in the sol, and more particles per unit time are able to collide by diffusion with the surface of the cell. Manual vortex mixing creates fluid shear within the reaction liquid. Particles that randomly cross shear lines by Brownian motion collide with cells moving at different collective, unidirectional velocities and hence more particles per unit time are able to collide by diffusion with the surface of the cell.

Neither centrifugation nor manual vortex-mixing are desirable methods for reaction rate enhancement. Centrifugation requires a high skill level to perform and adds additional equipment expense to the cost of manufacturing a system to perform the assay that is part of the subject matter of this invention. Manual vortex-mixing is highly dependent on operator skill, and is highly variable in end result from operator to operator. It is carried out by holding a test tube containing the reaction mixture in a loose finger grip near the top, and pressing the bottom of the tube onto a pressure-activated rotating eccentric wheel. The bottom of the test tub describes a circular arc while the top remains relatively stationary. The angle at which the operator holds the tube, the pressure exerted on the wheel, and number of total revolutions, all determine the rate of reaction. The following example illustrates the application of the present invention in overcoming the shortcomings of these prior art methods, while enhancing the rate of particle binding to the target cells.

Receptors are finite in size and are generally spaced randomly over the surface of the cell, which means that not all collisions between the particle and the cell will result in binding. The kinetics of binding under these circumstances has been studied by Berg and Purcell (H. C. Berg and E. M. Purcell, "The Physics of Chemoreception", Biophysical Journal, 20, 193 (1977)), and the following equations can be used to predict the rate at which particles would bind to the cell surface.

$$J = J_{max}[Ns/(Ns+\pi a)]$$

$$J_{max} = 4\pi a D c_p$$

J=Rate of particle binding to a cell (number per second)
$J_{max}$=Maximum rate of particle binding
N=Number of receptors on the cell
s=Radius of the receptor (cm)
a=Cell radius (cm)
D=Diffusion coefficient for particle in water (cm$^2$/sec)
$c_p$=Concentration of particles (number per cm$^3$)

According to this equation, if one wishes to increase the rate of binding of particles to cells of a specific type, then one can increase the particle concentration, $c_p$, or the diffusion coefficient of the particle, D.

As an example, consider gold sols with a particle diameter of 80 nm (0.08µ or 8E-6 cm). The diffusion coefficient at temperature of 20 C for a particle of this size can be calculated and is 5E-8 cm$^2$/sec. A typical protein receptor has a radius of about 50 Angstrom units or 5E-7 cm. A cell such as a lymphocyte has a radius of 5µ or 5E-4 cm. There are ~50,000 CD4 receptors on the surface of a lymphocyte. Combining these values in the above equation one can calculate that:

$$J = (7E-11 \text{ cm}^3/\text{sec}) c_p.$$

With an undiluted stock solution of 80 nm gold sol, the particle concentration, $c_p$, is 8E11/cm$^3$ (30 Optical Density Units at 555 nm). With this concentration, and according to the above equation, J~50/sec. Therefore, the time required to cover all the approximate 50,000 CD4 receptor sites on a human T-lymphocyte should be about 15 minutes.

Increasing the reaction temperature from 20 C to 37 C increases the particle diffusion coefficient (*Physics with Illustrative Examples from Medicine and Biology* (Second Edition), George B. Benedek and Felix M. H. Villars, AIP Press, p 123 Statistical Physics). The particle diffusion coefficient is a linear function of the Kelvin temperature, therefore increasing the reaction temperature from 20 C to 37 C is only a 5% increase on the Kelvin scale (293K to 310K). Thus the predicted reaction time to saturate the CD4 sites on a human T-lymphocyte remains at approximately 15 minutes. While these predicted times are useful for a rapid diagnostic test, they proved to be grossly false when evaluated in practice.

In practice, the time to saturate the sites on a human T-lymphocyte was found to be in excess of 3 hours which is in marked disagreement with the predictions of the Berg and Purcell model. The source of this significant discrepancy lies in the fact that both the human T-lymphocyte and the gold particle have like surface charges. Both are negatively charged, and hence low energy collisions are prevented by Coulombic forces of repulsion.

We have found that the addition of hexadimethrine bromide to the reaction solution accelerates the reaction significantly by neutralizing the Coulombic forces that slow the reaction.

Figure 7A:
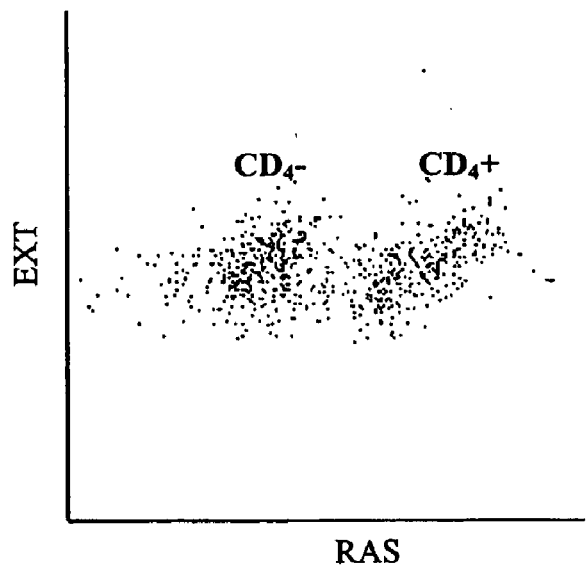
FIG. 7 are diagrammatic representations of the comparative resolution of CD4+ lymphocyte clusters, (a) after 3 hour incubation at 37 degrees centigrade without accelerant, and (b) after a 5 minute incubation at 37 degrees centigrade with 0.1% hexadimethrine bromide.
Figure 7B:
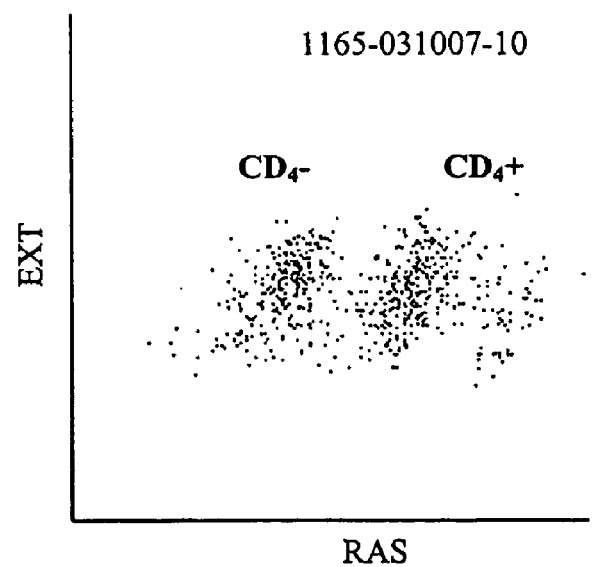

When anti-CD4 antibody (Serotech, Inc.) was coated to 65 nm colloidal gold particles and reacted with whole blood at 37 C, a distinct flow cytometry cluster of CD4 positive cells was created with multi-angle light scatter detection by EXT and RAS after an incubation time of 3 hours, and these could be accurately enumerated (FIG. 7a). When hexadimethrine bromide was included in the reaction solution at a concentration of 0.05% to 1.0% by volume, the time to create an equivalently distinct cluster of CD4 positive cells was reduced to approximately 4 minutes (FIG. 7b). No centrifugation or vortex-mixing were employed, thus the assay cost is contained and subjectivity is removed. This accelerated reaction is important for the ability to report patient results in settings where rapid medical action is required. These settings include remote regions where patients cannot readily communicate with the clinic if results are not ready before the patient must start the return journey to their home.

Hexadimethrine bromide is a polycationic surfactant that with known ability to coat negatively charged surfaces and reduce or neutralize negative charge. Tien et al (Joe Tien, Andreas Terfort, and George M. Whitesides, *Microfabrication Through Electrostatic Self-Assembly, Langmuir* 1997, 13, 5349-5355) have demonstrated that when $PO_3H^-$-termination, or $CO_2^-$-termination, or polyvinylsulfonate-coating was used to create negatively charged gold particles, immersion in hexadimethrine bromide solutions of 20 mM for 10 to 30 minutes reduced the negative charge.

The interior of a colloidal gold particle is electrically neutral, but the surface is negatively charged since the particles are "grown" chemically from gold chloride solutions. Unreacted gold chloride resides on the particle surface, imparting a net negative charge to the particle. While extremely important in maintaining a colloidal particle in stable suspension over long storage times, these charges cause repulsion from the negatively charged cell surface and retard the desired binding reaction.

Other applications in which hexadimethrine bromide has been used to reduce surface charge are as a coating on capillary electrophoresis tubes and in red cell blood group assays. In a red cell blood grouping assay application (for blood transfusion), free antibodies against a specific red cell blood group surface antigen are added to a suspension of red cells. The antibodies bind to the red cells, but being negatively charged the red cells repel and the antibody is not able to make a bridge between two red cells. With the addition of hexadimethrine bromide, the cell charge is reduced, and the antibody can bridge the distance between two cells. This results in the agglutination of red cells, which is an end point that is easily detectable by the unaided eye. Agglutination in the presence of hexadimethrine bromide provides a rapid blood grouping assay.

Other cationic surfactants that are effective in coating capillary tubes and therefore would be candidates for use in the present assay in the present invention are:
1. Decamethonium bromide
2. Polydiallyldimethylammonium chloride
3. Hexadecyltrimethylammonium bromide C) Apparatus for Multi-Angle Light Scatter from Surface-Bound Colloidal Particles and Multi-Angle Light Scatter from Whole Cells to Selectively Identify and Quantify Cell Types:

Each ORP acts as a point source of scattered light. Since the incident light is coherent, the phase of the excitation at each point source is fixed by the position of the ORP. Under these conditions, the reradiated coherent light is additive in certain directions and subtractive in others.

If the average spacing between randomly placed ORP's is $\Lambda$, the incident wavelength is $\lambda$, the refractive index of the medium is n, then the angle $\theta$ between the incident beam and the direction for which most of the light scatter occurs can be derived from the light scatter theory of granular media as sin $(\theta/2)=\lambda 2n\Lambda$ (Hansen, W. P, et al, Light Scatter as an Adjunct to Cellular Immunofluorescence in Flow Cytometric Systems, J. Clin. Immunology, vol 2, No. 3, July Supplement, 1982.).

The smallest spacing that causes coherent addition of light is $\Lambda=\lambda/2n$ and this causes scatter at 180 degrees (backscatter). Spacings that are smaller than this do not produce coherent addition of scattered light, and only result in weak omni-directional Rayleigh scattering.

One can now calculate the direction of light scatter for ORP's of different spacing on the surface of a cell. For example with $\lambda=0.635\mu$ (a semiconductor diode laser), and n =1.3 (water), ORP spacing and scattering angle pairs can be calculated once the spacing between ORP's is known.

As an example consider the CD4 subset of lymphocytes. There are ~50,000 CD4 binding sites on a CD4 lymphocyte. A CD4 lymphocyte has a diameter of ~10µ, therefore the average spacing between ORP's that are bound to CD4 receptors is about $\Lambda_o =0.08\mu$ when there is 100% coverage of the receptors. This spacing is too small to give coherent light scatter. The spacing of next nearest neighbor pairs ($2\Lambda_o$) is also too small, but the next-next nearest neighbors ($3\Lambda_o$) are spaced at 0.24µ and this gives 180 degree light scatter. The table below shows that most of the coherently scattering ORP's scatter light at very wide angles.

| ORP Spacing | Scattering angle, $\theta$ |
|---|---|
| $7\Lambda_o = 0.56\mu$ (~20% of coherent ORP's) | 51 deg |
| $6\Lambda_o = 0.50\mu$ (~30% of coherent ORP's) | 58 deg |
| $5\Lambda_o = 0.40\mu$ (~40% of coherent ORP's) | 75 deg |
| $4\Lambda_o = 0.32\mu$ (~60% of coherent ORP's) | 100 deg |
| $3\Lambda_o = 0.24\mu$ (~100% of coherent ORP's) | 180 deg |

Light scattered in the forward direction (12 degrees or less) by gold particles bound to the cell surface is very weak compared to light they scatter at right angles or backward angles. Forward scattered light may be affected only by the cell (lymphocyte in this example) itself and not by the binding of gold particles to the cell surface. On the other hand, light scattered at right angles or backward angles is affected by gold particles bound to the cell surface. Under this hypothesis, lymphocytes might be identified by forward angle light scatter, monocytes can be rejected, and this identification can be used as a Boolean "gate" to enable counting of CD4 positive lymphocytes by wide angle and backward angle light scatter. The hypothesis was verified in the example that follows.

Nearly 100% of the light scattered by a lymphocyte without ORP's on the surface is contained within a narrow cone of forward scattered light with half angle of about 5 degrees (Hansen, W. P, et al, Light Scatter as an Adjunct to Cellular Immunofluorescence in Flow Cytometric Systems, J. Clin. Immunology, vol 2, No. 3, July Supplement, 1982.). Referring to the table above, a detector at 90 degrees to the incident beam with an acceptance cone of approximately 45 degrees to 180 degrees would see very low background scatter from the lymphocyte itself, and might be sensitive to ORP scatter.

To show this experimentally, light scatter from a sample of human white blood cells was simultaneously analyzed on a light scatter flow cytometer after red cell lysis. The multi-angle light scatter detectors were designated as; FSL (low angle forward scatter from 0.5 degrees to 2 degrees), FSH (high angle forward scatter from 9 degrees to 12 degrees), EXT (total light blocked) and RAS (right angle scatter from 45 degrees to 135 degrees) (FIG. 4).

Figure 8A:
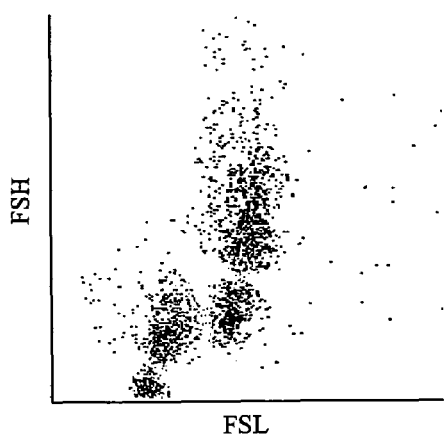
FIG. 8 are diagrammatic representations of comparative positions of lymphocyte clusters (a) using FSH versus FSL with a nonbonding control reaction and (b) using FSH versus FSL when anti CD4 conjugated colloidal gold binds to the lymphocyte surface.
Figure 8B:
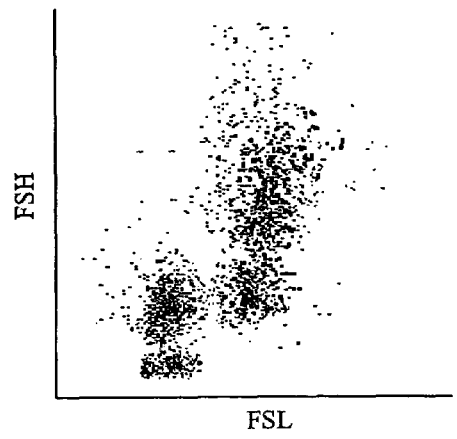

FIG. 8 shows four distinct clusters in a plot of FSH versus FSL. Unlysed red cells and platelets lie in the lower left most cluster. Lymphocytes lie in the left-hand cluster above the unlysed red cells and platelets, monocytes are in the cluster to the right of the lymphocytes, and granulocytes are in the upper cluster. FIG. 8a shows the cluster positions after incubation with 80 nm colloidal gold conjugated with a non-binding goat anti-mouse antibody. FIG. 8b was obtained by incubating 80 nm colloidal gold conjugated to anti-CD4 monoclonal antibody. It shows that the lymphocyte cluster showed no change in either FSL or FSH as a result of ORP binding to lymphocytes. This result is in agreement with the above hypothesis that little or no change would occur in lymphocyte light scatter at FSL and FSH angles when ORP's were bound to the CD4 receptors. Similar results are obtained when a new parameter called "time of flight" (TOF) is substituted for FSL (FIG. 9). TOF is used to measure the time it takes a cell to cross the laser line focus in a flow cytometer. The timing gate is initiated and terminated from the EXT signal. The use of FSH versus TOF is preferred for the practice of this invention.

Figure 10A:
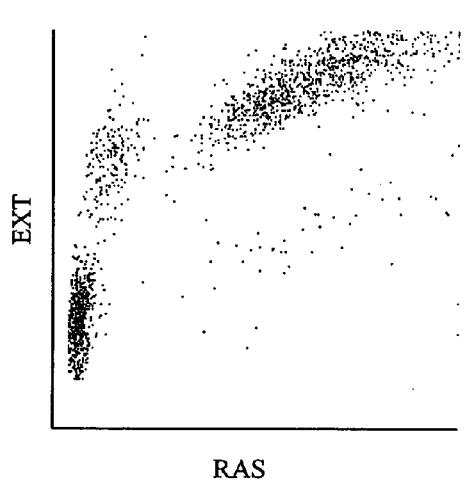
FIG. 10 are diagrammatic representations of plots of RAS versus EXT; wherein (a) granuloctyes are in the cluster to the upper right, monocytes are in the cluster to the left of the granulcotyes, and lymphocytes are in one cluster below the monocytes and granulocytes in the absence of colloidal gold binding; and (b) in the presence of anti-CD4 conjugated colloidal gold binding there are two lymphoctye clusters instead of one, the CD4 positive lymphocytes that are labeled with colloidal gold are in the right hand lymphocyte cluster.
Figure 10B:
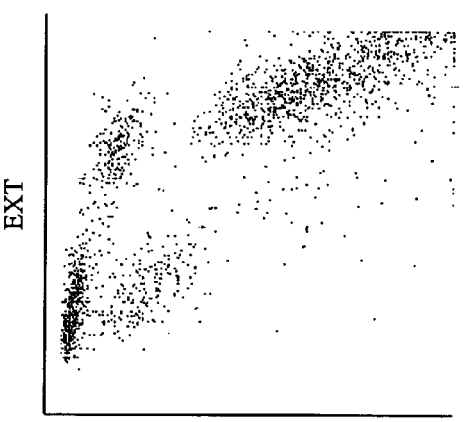

Referring to FIG. 10, which shows a plot of RAS versus EXT. Granulocytes are in the cluster to the upper right, monocytes are in the cluster to the left of the granulocytes, and lymphocytes are in one cluster below the monocytes and granulocytes in the absence of colloidal gold binding (FIG. 10a). In the presence of anti-CD4 conjugated colloidal gold binding there are two lymphocyte clusters instead of one as shown in FIG. 10b. The CD4 positive lymphocytes that are labeled with colloidal gold are in the right hand lymphocyte cluster. This is in agreement with the hypothesis that RAS will be affected by gold particles bound to the lymphocyte cell surface, and that CD4 positive lymphocytes can be enumerated.

This example illustrates one aspect of the current invention which is to combine information from multi-angle light scatter from cells themselves with information from multi-angle light scatter from colloidal gold particles bound to specific cell surface markers in order to identify and enumerate specific cell types.

Figure 11:
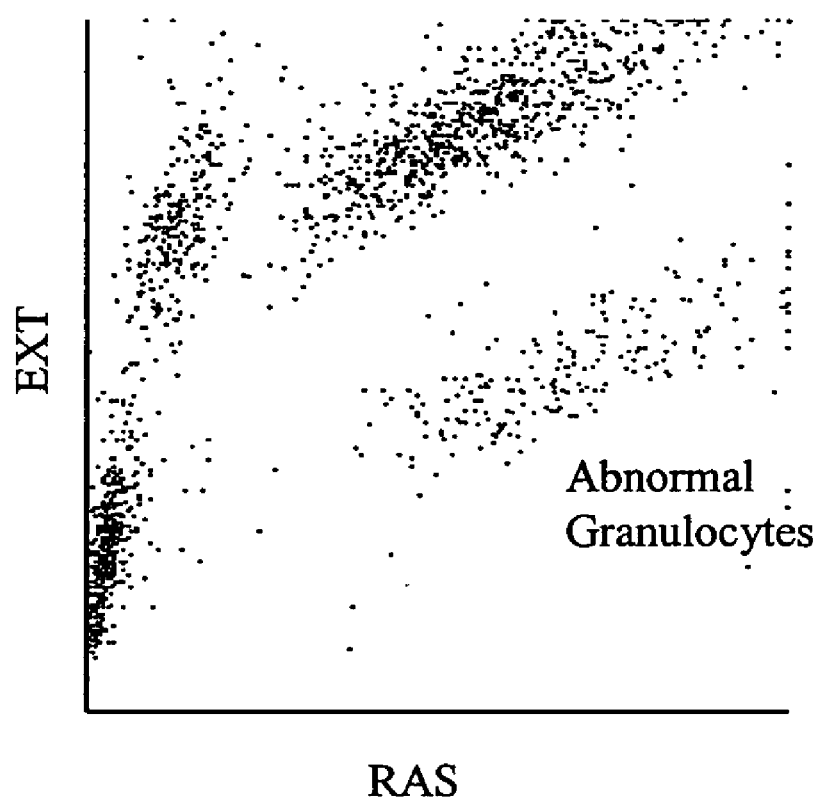
FIG. 11 is a diagrammatic representation of a plot of RAS versus EXT; wherein abnormal granulocyte cluster interferes with non-gated CD4 positive lymphocyte counting.

Referring to FIG. 11, the value of Boolean gating of lymphocytes is demonstrated. The blood sample used in this case contained granulocytes with abnormal EXT values. These abnormal granulocytes appear in the same region on a plot of EXT versus RAS as do the CD4 positive lymphocytes. Such overlap would invalidate the CD4 count. This serious error is avoided by first using the Boolean gate that, "only those cells that lie within the lymphocyte cluster for FSH versus FSL (or EXT)" are admitted by the gate, and then only cells passing through that gate are used in the EXT versus RAS plot.

Figure 12:
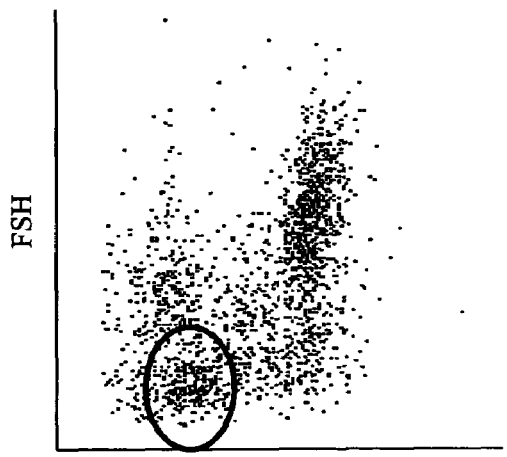
FIG. 12 are diagrammatic representations of plots illustrating (a) gating lymphocytes by FSH versus TOF; (b) interference between CD4 lymphocytes and abnormal granulocytes in an un-gated dot plot by RAS versus EXT; and (c) no interference using gated dot plot by RAS versus EXT.
Figure 12:
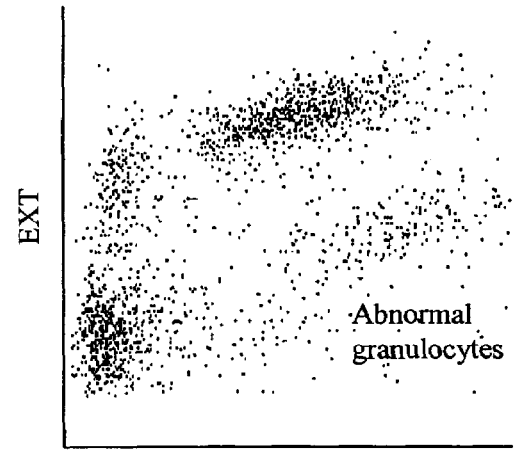
Figure 12:
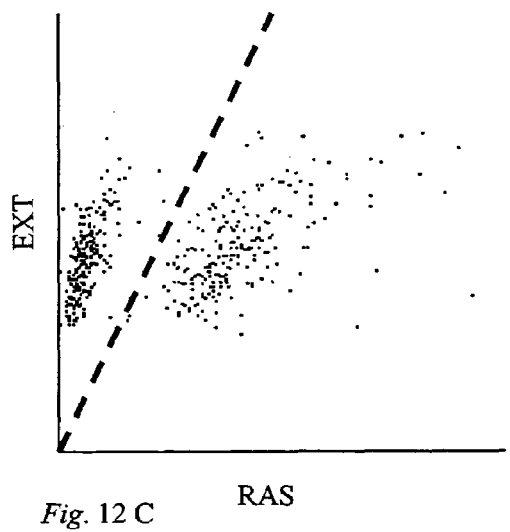

An example is shown in FIG. 12. Abnormal granulocytes interfered with un-gated CD4 lymphocyte counting, and produced an incorrectly elevated CD4 count. When the Boolean gate was applied, the interfering granulocytes were eliminated, and the correct CD4 count was obtained. Avoiding such interference is extremely important with HIV positive patients whose actual CD4 lymphocyte count is low and is near the level where decisions to start therapy must be made before the CD4 count drops to the point where opportunistic infections endanger the life of the patient.

This gating technique can be extended to other cell groups. For example if monocytes are labeled with ORP's they shift onto the very dense granulocyte cluster in EXT-RAS space. The small number of shifted monocytes would be very difficult to resolve against the high granulocyte background. By gating on monocytes in FSL-FSH space and viewing the shifted monocytes in EXT-RAS space, the granulocytes are eliminated from the background. The same gating techniques can be applied to the identification of other lymphocyte subsets such as CD8 positive or CD3 positive lymphocytes, or natural killer cells.

D) Components Used in the Present Invention:

Optically Resonant Particles (ORP's):

The class of materials suitable for the present invention are those for which the real part n of the refractive index approaches zero and the imaginary part of the refractive index, k approaches $\sqrt{2}$ at one or more wavelengths, $\lambda_R$. Such wavelengths are termed "resonant wavelengths" or "resonances" for the purposes of this invention. There is a distinct extinction spectrum maximum at the resonant wavelength for single, substantially spherical, colloidal particles that are composed of material fulfilling the above requirements.

The colloidal material preferably contains particles including metals and metal compounds, such as metal oxides, metal hydroxides and metal salts. Preferred examples of metals include gold, platinum, silver and copper. Gold is highly preferred. Methods of production of colloidal gold of the desired range of particle diameters, and methods for coating metal particles with proteins, are described generally in European patent application 426,300, Roth, J., "The Colloidal Gold Marker System for Light and Electron Microscopy Cytochemistry", in Bullock, G. R. et al., Techniques in Immunocytochemistry 2:217 (1983), in Horisberger, M., SEM 11:9 (1981), in Weiser, H. B., Inorganic Colloid Chemistry, J. Wiley, N.Y. 1931, p. 1, in Leuvering, J. H. W., U.S. Pat. No. 4,313,734, and in Frens, G., Nature, Physical Science, 241:20 (1973), all of which are incorporated by reference.

The preparation of ORP's useful in the methods of the present invention are well-known to those skilled in the art, including U.S. Pat. Nos. 6,413,786; 6,200,820; 5,939,021; 5,589,401, 5,851,777, 5,369,037, and 5,286,452 all incorporated herein by reference in their entirety.

Cell Specific Binding Compounds:

The ORP's used in the methods of the present invention are conjugated to cell specific binding compounds. Suitable cell specific binding compounds for use in the present invention include antibodies.

The term "antibody" encompasses monoclonal antibodies, polyclonal antibodies, multispecific antibodies (e.g., bispecific antibodies), and antibody fragments, so long as they exhibit the desired biological activity or specificity. "Antibody fragments" comprise a portion of a full length antibody, generally the antigen binding or variable region thereof. Examples of antibody fragments include Fab, Fab', F(ab')$_2$, and Fv fragments.

Antibodies raised against cell specific surface molecules, such as receptors, are produced by immunizing a host animal with a cell surface receptor protein or an antigenic fragment thereof. Suitable host animals for injection of the protein immunogen include, but are not limited to, rabbits, mice, rats, goats, and guinea pigs. Various adjuvants may be used to increase the immunological response of the immunogen or antigen (i.e., the cell surface receptor protein or peptide) in the host animal. The adjuvant used depends, at least in part, on the host species. For example, guinea pig albumin is commonly used as a carrier for immunizations in guinea pigs. Such animals produce heterogeneous populations of antibody molecules, which are referred to as polyclonal antibodies and which may be derived from the sera of the immunized animals. Such sera may be used directly, or the specific antibodies desired can be purified from the sera, using methods well known to those of skill in the art.

Antibodies are also prepared using an oligopeptide having a sequence which is identical to a portion of the amino acid sequence of a cell surface receptor protein isoform. Preferably the oligopeptide has an amino acid sequence of at least five amino acids, and more preferably, at least 10 amino acids that are identical to a portion of the amino acid sequence of a cell surface receptor protein. Such peptides are conventionally fused with those of another protein such as keyhole limpet hemocyanin and antibody is produced against the chimeric molecule. Such peptides can be determined using software programs, for example the MACVECTOR™ program, to determine hydrophilicity and hydrophobicity and ascertain regions of the protein that are likely to be present at the surface of the molecule.

The term "monoclonal antibody" as used herein, refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site, also called epitope. Furthermore, in contrast to conventional (polyclonal) antibody preparations, which typically include different antibodies directed against different determinants (epitopes), each monoclonal antibody is directed against a single determinant on the antigen.

The monoclonal antibodies to be used in accordance with the present invention may be made by the hybridoma method, first described by Kohler and Milstein (Nature 256:495-497, 1975), in which case the hybridoma cell lines that are obtained secrete the monoclonal antibodies during growth. As is known in the art, hybridomas that secrete monoclonal antibodies are made by injecting mice with the desired antigen. The antigens frequently are peptide antigens which are chosen using similar procedures as described above for selection of peptide antigens for making polyclonal antibodies. After the antigens have been injected into the mice, spleen cells are taken from the immunized mice and are fused to myeloma cells. Clones of fusion cells are then obtained and are screened for production of anti-cell surface receptor antibodies.

Various immunoassays may be used for screening to identify antibodies having the desired specificity. These include protocols which involve competitive binding or immunoradiometric assays and typically involve the measurement of complex formation between the respective cell surface receptor protein and the antibody.

In order to grow the hybridoma cell lines and obtain the secreted antibodies, the hybridoma cell lines may be grown in cell culture and culture medium containing the monoclonal antibodies collected. Alternatively, the hybridoma cell lines may be injected into, and grown within, the peritoneal cavity of live animals, preferably mice. As the hybridoma cell lines grow within the peritoneal cavity of the animal, the monoclonal antibodies are secreted. This peritoneal fluid, called "ascites," is collected using a syringe to obtain the monoclonal antibodies. Such antibodies may be of any immunoglobulin class including IgG, IgM, IgE, Iga, IgD and any class thereof.

Antibody preparations may be isolated or purified. An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody may be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies immunospecific for cell surface receptor are useful for identifying cells or tissues in accordance with the methods of the present invention. The identification and quantification of specific cells and tissues are useful in numerous diagnostic/prognostic methods for identifying or monitoring equally numerous diseases and disorders, including those related immunology, oncology, cardiology and neurology.

The ORP's used in the methods of the present invention are conjugated to cell specific binding compounds. Factors important in preparing ORP/cell specific binding compound conjugates include ORP composition and concentration, pH, ionic strength, as well as the composition and concentration of the cell specific binding compound. Optimization of these factors is required to produce each particular ORP/cell specific binding compound conjugate and optimization is readily accomplished by one skilled in the art.

Alternatively, ORP's can be coated with the binding protein streptavidin (MW 65,000). Coating is performed by passive adsorption at room temperature. Subsequently, the streptavidin-coated ORP's are contacted with a biotin labeled cell specific binding compound, thus achieving ORP/cell specific binding compound conjugation.

Cationic Surfactants:

Cationic surfactants are generally positively charged quaternary ammonium compounds. In the context of the present invention, they act to accelerate the reaction between ORP's and and cell surface receptors significantly by neutralizing the negative Coulombic forces that slow the reaction, thereby avoiding the currently necessary step(s) of centrfugation or vortexing. A preferred cationic surfactant useful in the methods of the present invention is hexadimethrine bromide. Other cationic surfactants that are effective for use in the present invention include, but are not limited to, decamethonium bromide, polydiallyldimethylammonium chloride, hexadecyltrimethylammonium bromide, tetramethyl ammonium, tetrapropyl ammonium, tetrabuytl ammonium, cetyltrimethyl ammonium and myristylmethyl ammonium. (generally see, Cationic Surfactants: Physical Chemistry; Surfactant Science Series, Vol. 37; Editors: Rubingh, D. N and Holland, P. M.; Dekker Publishing; 1991; ISBN 0824783573).

The examples herein are given for the purpose of illustrating various embodiments of the invention and are not meant to limit the present invention in any fashion. All documents mentioned herein are incorporated by reference in their entirety.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

We claim:

1. A method of treating a sample containing cell surface receptors to increase the rate of binding between cell surface receptors and antibody associated with Optically Resonant Particles (ORP's) that allows binding of ORP's to cell surface receptors comprising the steps of: 1) obtaining a sample containing cell surface receptors and 2) simultaneously contacting a) the sample, b) negatively charged ORP's associated with antibody; and c) an aliquot of cationic surfactant, wherein the cationic surfactant neutralizes the negatively charged ORP's.

2. A method of claim 1 wherein the cationic surfactant is selected from the group consisting of decamethonium bromide, hexadimethrine bromide, polydiallyldimethylammonium chloride and hexadecyltrimethylammonium bromide.

* * * * *